US011807844B2

(12) United States Patent
Kamei et al.

(10) Patent No.: US 11,807,844 B2
(45) Date of Patent: Nov. 7, 2023

(54) MICROFLUID DEVICE AND THREE-DIMENSIONAL MICROCULTURE METHOD FOR CELL

(71) Applicants: KYOTO UNIVERSITY, Kyoto (JP); Ushio Denki Kabushiki Kaisha, Toyota (JP)

(72) Inventors: Kenichiro Kamei, Kyoto (JP); Yong Chen, Kyoto (JP)

(73) Assignees: KYOTO UNIVERSITY, Kyoto (JP); Ushio Denki Kabushiki Kaisha, Tokyo (JP)

( * ) Notice: Subject to any disclaimer, the term of this patent is extended or adjusted under 35 U.S.C. 154(b) by 252 days.

(21) Appl. No.: 17/406,916

(22) Filed: Aug. 19, 2021

(65) Prior Publication Data
US 2022/0119747 A1 Apr. 21, 2022

Related U.S. Application Data

(63) Continuation of application No. 15/121,553, filed as application No. PCT/JP2015/055178 on Feb. 24, 2015, now Pat. No. 11,130,935.

(30) Foreign Application Priority Data

Feb. 25, 2014 (JP) ................. 2014-034166

(51) Int. Cl.
| C12M 1/12 | (2006.01) |
| C12M 3/06 | (2006.01) |
| C12M 1/42 | (2006.01) |
| C12N 1/04 | (2006.01) |
| C12N 5/074 | (2010.01) |
| C12N 5/00 | (2006.01) |
| B33Y 80/00 | (2015.01) |

(52) U.S. Cl.
CPC ............ *C12M 25/14* (2013.01); *C12M 23/16* (2013.01); *C12M 35/08* (2013.01); *C12N 1/04* (2013.01); *C12N 5/0062* (2013.01); *C12N 5/0696* (2013.01); *B33Y 80/00* (2014.12); *C12N 2500/50* (2013.01); *C12N 2501/999* (2013.01); *C12N 2513/00* (2013.01); *C12N 2521/00* (2013.01); *C12N 2523/00* (2013.01); *C12N 2533/30* (2013.01); *C12N 2539/10* (2013.01)

(58) Field of Classification Search
CPC ...... C12M 25/14; C12M 23/16; C12M 35/08; C12N 1/04; C12N 5/0062; C12N 5/0696; C12N 2500/50; C12N 2501/999; C12N 2513/00; C12N 2521/00; C12N 2523/00; C12N 2533/30; C12N 2539/10; B33Y 80/00
See application file for complete search history.

(56) References Cited

U.S. PATENT DOCUMENTS

2011/0256574 A1* 10/2011 Zhang ................... C12M 23/16
435/325

* cited by examiner

*Primary Examiner* — Michael L Hobbs
(74) *Attorney, Agent, or Firm* — Kenichiro Yoshida

(57) ABSTRACT

The invention provides a microfluidic device comprising at least one cell culture chamber, the at least one cell culture chamber being connected to at least two openings, the device being configured to supply at least one physiologically active substance from at least one of the openings to the at least one cell culture chamber in such a manner as to form a concentration gradient or concentration gradients in the at least one chamber when cells and a hydrogel are introduced into the at least one cell culture chamber to culture the cells in a 3D-gel medium.

34 Claims, 10 Drawing Sheets

MICROFLUID DEVICE AND THREE-DIMENSIONAL MICROCULTURE METHOD FOR CELL

TECHNICAL FIELD

The present invention relates to a microfluidic device and a 3D cell microculture method.

BACKGROUND ART

The function of a cell in vivo is regulated in the extracellular microenvironment. The extracellular microenvironment consists mainly of (i) soluble factors such as growth factors, vitamins, and gas molecules, (ii) insoluble factors such as the stiffness of extracellular matrix proteins, and (iii) cell-cell interaction. These factors regulate the function of a cell while being intricately and strictly regulated. More specifically, in order to freely regulate the function of a target cell, such as a human ES cell and a human iPS cell, it is indispensable to freely regulate this extracellular microenvironment.

However, the regulation occurs in an extremely small environment on a micrometer scale, and the traditional experimental cell culture technique using a 2D environment in a culture dish or a plate cannot reproduce the small environment. Thus, there is a demand for a technique for creating an experimental 3D cell culture environment, which has been difficult to realize.

Traditional experimental human ES/iPS cell culture techniques have been performed in a 2D environment such as a culture dish (Non-patent Literature 1 and 2).

However, cells are present in a 3D environment in ordinary circumstances, and cannot express the original function in the 2D environment. In tissue engineering using human ES/iPS cells as well, it is very important to arrange a 3D environment.

Size is also a very important factor. Cells in vivo are regulated in a microenvironment on a micrometer scale, for example, by the concentration gradients of soluble factors and the solidity of the extracellular substrate. It has been difficult for traditional techniques to regulate these factors. As a matter of course, it has been almost impossible to exhaustively analyze these factors.

CITATION LIST

Non-Patent Literature

Non-patent Literature 1: K. Kamei et al. Lab Chip, 9 (4), 555-563(2009)
Non-patent Literature 2: K. Kamei et al. Lab Chip, 10 (9), 1113-1119 (2010)

SUMMARY OF INVENTION

Technical Problem

An object of the present invention is to provide a microfluidic device suitable for culturing cells in a 3D environment and a 3D microculture method that enables the regulation and the analysis of function of cells, in particular, pluripotent stem cells.

Solution to Problem

The present invention developed a novel 3D cell microculture device for human ES cells and human iPS cells by using a microfluidic device. This microfluidic device enables the culture of an extremely small amount of cells, and can easily establish a 3D culture.

Traditional culture and experimental techniques for the human ES cells and human iPS cells are performed in a 2D environment using a culture dish or a plate. However, the cells in vivo are regulated in a 3D microenvironment, and cannot fulfill the original function in the 2D environment. Thus, there has been a demand for a technique for creating an experimental 3D cell culture environment, which has been difficult to create by traditional techniques.

The present inventors have been engaged in the development of a cell culture assay using a microfluidic device. The present invention has enabled a 3D culture by creating a 3D-like microenvironment using a microfluidic device, and using a highly biocompatible hydrogel as a cell support carrier.

The present invention is a novel technique that has solved the problems of the existing methods and techniques. The following describes the features of the present invention in a preferable embodiment.

(1) Development of a 3D culture method for cells, particularly for pluripotent stem cells, such as human ES/iPS cells, using a microfluidic device.
(2) Creation of a 3D environment in a human ES/iPS cell culture method using a hydrogel
(3) Simplification of cell introduction into and extract from the microfluidic device and a decrease in damages to the cells by using a phase transition hydrogel Specifically, the present invention provides the following microfluidic device and 3D microculture method. Item 1.

A microfluidic device comprising at least one cell culture chamber, the at least one cell culture chamber being connected to at least two openings, the device being configured to supply at least one physiologically active substance from at least one of the openings to the at least one cell culture chamber in such a manner as to form a concentration gradient or concentration gradients in the at least one cell culture chamber when cells and a hydrogel are introduced into the at least one cell culture chamber to culture the cells in a 3D-gel medium.

Item 2.

The microfluidic device according to item 1, wherein the hydrogel is formed inside the at least one cell culture chamber.

Item 3.

The microfluidic device according to item 1 or 2, wherein a channel or channels connecting the at least one of the openings to the at least one cell culture chamber are narrower than the diameter of the at least one cell culture chamber.

Item 4.

A 3D cell microculture method comprising the steps of introducing cells and a fluidized hydrogel into the at least one cell culture chamber of the microfluidic device according to any one of items 1 to 3;
converting the hydrogel into a gel; and
supplying at least one physiologically active substance from the at least one of the openings in such a manner as to form a concentration gradient or concentration gradients inside the at least one cell culture chamber to culture the cells in the presence of the at least one physiologically active substance.

Item 5.

The 3D cell microculture method according to item 4, wherein the cells are pluripotent stem cells.

Item 6.

The 3D cell microculture method according to item 4, wherein the cells are human pluripotent stem cells.

Item 7.

The 3D microculture method according to any one of items 4 to 6, wherein multiple physiologically active substances are supplied into the at least one cell culture chamber in such a manner as to form concentration gradients.

Advantageous Effects of Invention

The present invention enables a 3D cell microculture of cells, including pluripotent stem cells such as ES cells and iPS cells, using a microfluidic device. This microfluidic device enables a cell culture using an extremely small amount of cells, and can also easily establish a 3D culture.

Because the microfluidic device according to the present invention can supply many different physiologically active substances to a 3D gel while forming respective concentration gradients thereof, the device can exhaustively screen various physiologically active substances for their action on the differentiation and functional regulation of cells, particularly pluripotent stem cells.

The present invention is characterized in that the invention has created an extracellular microenvironment, which so far has been impossible to create in vitro, by using a microfluidic device, and developed a device for evaluating the cell response to the extracellular microenvironment. Because the functions of mammal cells, including human pluripotent stem cells, are strictly regulated in vivo by the extracellular microenvironment, it has been essential for the advancement of tissue engineering, cell transplant therapy, or regenerative medicine to know the regulation mechanism. The present development has overcome this problem, and can greatly contribute to the commercial viability of mammal pluripotent stem cells including human pluripotent stem cells.

The device developed by the present invention can also be applied to drug discovery screening. Traditional cell-using drug discovery screening involves cells cultured in a 2D environment on a plate. However, the functional expression of cells requires the creation of a 3D environment; i.e., the cell response to a medicinal substance as a matter of course differs between a 2D culture and a 3D culture. The present invention also successfully achieved high throughput with a 3D culture, thus enabling a 3D culture of cells including human pluripotent stem cells, and drug discovery screening using the 3D culture.

This extracellular microenvironment is very important not only for human pluripotent stem cells but also for cancer stem cells.

Although the extracellular microenvironment has been suggested to be involved in the formation of cancer stem cells, it has been difficult to conduct a study on cancer stem cells in vitro. The 3D culture method of the present invention is applicable to the research of cancer stem cells, and can greatly contribute to the development of a basic remedy for cancer.

It is also an advantage of the present invention that the use of the microfluidic device can decrease the amount and cost of a single sample.

The use of the microfluidic device of the present invention can make it possible to stimulate cells physically and chemically at the same time, and to evaluate the cell response to the stimulations.

In a preferable embodiment of the present invention, the invention has already gained an edge over other research in the achievement of high throughput using a 3D culture of human pluripotent stem cells. This high throughput is also advantageous in that the inlets of the device are arranged in the positions so as to correspond to the wells of a conventional 96-well plate, enabling the use of conventionally used equipment, such as an autoinjector, without modification. This is also a feature of the invention that the use of the microfluidic device can reduce the amount and cost of a single sample. Whereas 100 to 200 µL of a sample is necessary per sample in the use of a conventional 96-well plate, the amount of sample required by the present invention is 10 µL, which reduces the amount of sample to ¹/₁₀, achieving commercial viability.

BRIEF DESCRIPTION OF DRAWINGS

FIG. 12 shows the sizes of human pluripotent stem cell spheres in gels with different degrees of solidity: too soft (45 mg mL$^{-1}$), soft (61 mg mL$^{-1}$), medium (75 mg mL$^{-1}$), and hard (91 mg mL$^{-1}$). Although the spheres in the too soft hydrogel can grow, the too soft gel cannot retain the cells.

DESCRIPTION OF EMBODIMENTS

Figure 1:
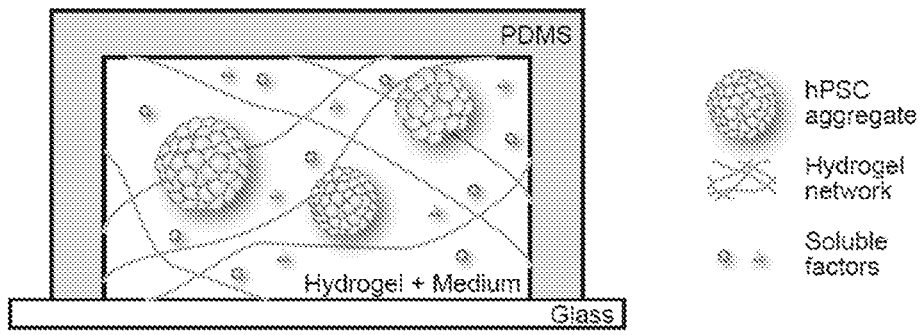
FIG. 1: A conceptual diagram of a 3D microenvironmental culture of human pluripotent stem cells in the present invention. A mixtured liquid of a fluidized hydrogel and human pluripotent stem cells is introduced into a microfluidic device to perform a 3D culture. Physiologically active substances necessary for the culture, such as growth factors, diffuse across the hydrogel, and are thereby supplied to the cells. Factors necessary for differentiation can also be optionally introduced.

The cells used in the present invention are animal cells, preferably vertebrate cells, and particularly preferably mammal cells. Examples of mammals include humans, mice, rats, dogs, monkeys, rabbits, goats, cows, horses, pigs, and cats, with humans being preferable. The cells are preferably pluripotent stem cells. Examples of pluripotent stem cells include stem cells, such as ES cells, iPS cells, mesenchymal stem cells, adipose stem cells, hematopoietic stem cells, neural stem cells, hepatic stem cells, and muscle stem cells. The pluripotent stem cells are preferably stem cells that can differentiate into multiple organs and tissues, such as ES cells and iPS cells. These stem cells are thought to require the concentration gradient(s) of one or multiple physiologically active substances in the process of differentiation. The use of the device and high throughput system according to the present invention enables the assay of substances important for the differentiation of stem cells.

Examples of physiologically active substances (stimulants) supplied, while forming a concentration gradient, include ions, such as calcium ion, potassium ion, magnesium ion, sodium ion, and chlorine ion; cytokines, such as hepatocyte growth factor (HGF), fibroblast growth factor (bFGF)/FGF-2, insulin, transferrin, heparin-binding EGF, gastrin, TGF-β, insulin-like growth factor (IGF-1), parathyroid hormone-related protein (PTHrP), growth hormone, prolactin, placental lactogen, glucagon-like peptide-1 (glucagon-like peptide-1), exendin-4, and KGF (keratinocyte growth factor); amino acids (e.g., Ala, Gly, His, Arg, Lys, Asp, Glu, Asn, Gln, Leu, Ile, Val, Phe, Tyr, Trp, Ser, Cys, Met, Pro, Thr, β-alanine, taurine, and ornithine); neurotransmission substances; carbohydrates (e.g., glucose, fructose, maltose, lactose, and sucrose); carboxylic acids (e.g., acetic acid, pyruvic acid, butyric acid, lactic acid, maleic acid, fumaric acid, malic acid, citric acid, tartaric acid, oxalic acid, and α-ketoglutaric acid); lipids (e.g., triglyceride, diglyceride, steroid, monoterpene, diterpene, sesquiterpene, phospholipid, and ganglioside), polyamines (e.g., spermidine and spermine); mucopolysaccharides; glucuronic acid; galacturonic acid; and pH adjusters. Examples of pH adjusters include acids, such as hydrochloric acid, nitric acid, sulfuric acid, and phosphoric acid; bases, such as sodium hydroxide, potassium hydroxide, lithium hydroxide, sodium carbonate, potassium carbonate, lithium carbonate, sodium hydrogen carbonate, potassium hydrogen carbonate, and lithium hydrogen carbonate; and buffer solutions, such as phosphoric acid buffer solutions, citric acid buffer solutions, acetic acid buffer solutions, and boric acid buffer solutions.

As the hydrogel material for the 3D culture, a variety of materials can be used that exhibit fluidity when cells are introduced into the chamber, and that can form a gel by a means such as the addition of other substances or heating (e.g., 37° C.) in the chamber.

Examples of hydrogels used in the present invention include chitosan gel, collagen gel, gelatin gel, peptide gel, fibrin gel, starch, pectin, hyaluronic acid, alginic acid, fibronectin, vitronectin, laminin, alginate, and fibroin. These can be used singly, or in a combination of two or more.

In a preferable embodiment, the hydrogel is preferably a material that undergoes phase transition in accordance with the temperature, for example, a gel that is a liquid at 15° C. or less, but becomes gelatinous in cell culture conditions (37° C.). When cells are introduced into the microfluidic device, cell manipulation is performed at low temperatures; when the cells are cultured, the temperature is increased to 37° C. to allow the material to form a gel. When the cells are collected after culture, the device is placed at low temperatures, allowing the gel to become a liquid. This makes it possible to remove the material.

Increasing the concentration of the gel can solidify the gel, whereas decreasing the concentration of the gel forms a soft gel. The correlation between the gel strength and the gel concentration of various hydrogel materials is known, and a person skilled in the art can readily determine the desired concentration.

In a preferable embodiment of the present invention, the gel used in the 3D culture is a temperature-sensitive gel material. Such a gel material is known, and Mebiol®, for example, can be used.

In a preferable embodiment of the present invention, usable gel materials are, for example, those capable of forming a gel when calcium ions, such as sodium alginate, are added. For example, a mixture liquid containing sodium alginate, a cell culture solution, and cells is introduced into the cell culture chamber, and then the chamber is impregnated with the solution of calcium ions introduced from the opening to fill the chamber with a gel. The gel can also be fluidized by removing calcium ions with a chelating agent.

In a preferable embodiment of the present invention, a usable hydrogel is, for example, one that forms a gel when heated at 37° C. for 30 minutes, such as collagen gel of Nitta Gelatin Inc. The collagen gel degrades when a collagenase acts on the gel. Thus, the cells can be taken out. Besides collagen, hydrogels that are degraded by enzyme activity, such as gelatin, hyaluronic acid, peptide, fibrin, and chitosan, can be preferably used.

The present invention can also examine the cell behavior affected by the solidity of the cellular environment. The diffusion of a physiologically active substance in a gel, unlike in a solution, is dramatically changed by the molecular weight of the substance. This phenomenon also occurs in vivo, and the microfluidic device of the present invention can reproduce the conditions in vivo.

The present invention is particularly useful as a 3D culture method for pluripotent stem cells, such as ES cells and iPS cells. The use of this method enables the regulation and analysis of the function of pluripotent stem cells of mammals, including humans (e.g., human ES cells and human iPS cells), which have been impossible by traditional methods.

Figure 2:
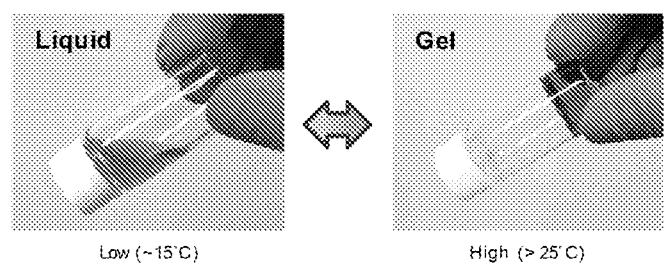
FIG. 2: A temperature-sensitive phase transition hydrogel (Mebiol®) used in the present invention. Changing the temperature enables the introduction of cells into a gel and the collection of the cells from the gel.
Figure 3:
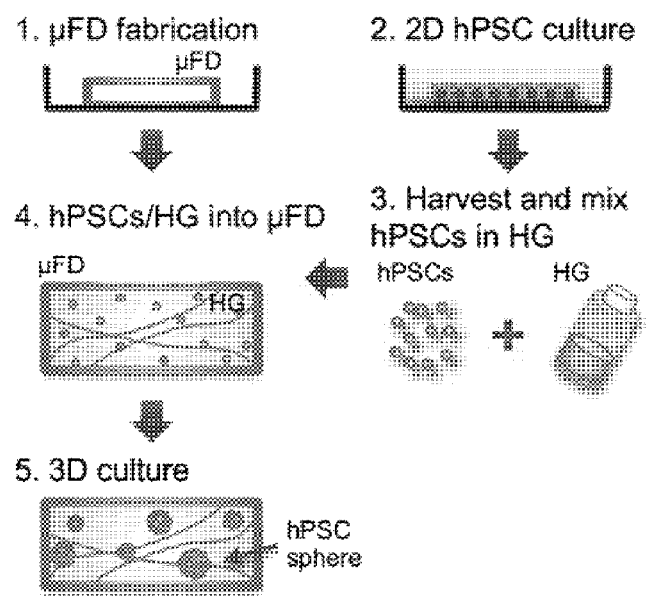
FIG. 3: An experiment operation procedure of the present invention. 1. Preparation of a microfluidic device (µFD). 2. A typical 2D culture of human pluripotent stem cells. 3. The human pluripotent stem cells are collected by an enzyme treatment or a physical treatment, and mixed with the hydrogel. 4. The mixture solution containing the human pluripotent stem cells and the hydrogel is introduced into the µFD, and the temperature is changed to solidify the hydrogel. 5. 3D culture. The medium is replaced as necessary.

FIGS. 1 and 3 show schematic diagrams of the 3D culture method using the microfluidic device of the present invention. FIG. 2 shows an example of the temperature-sensitive phase transition gel.

Figure 4:
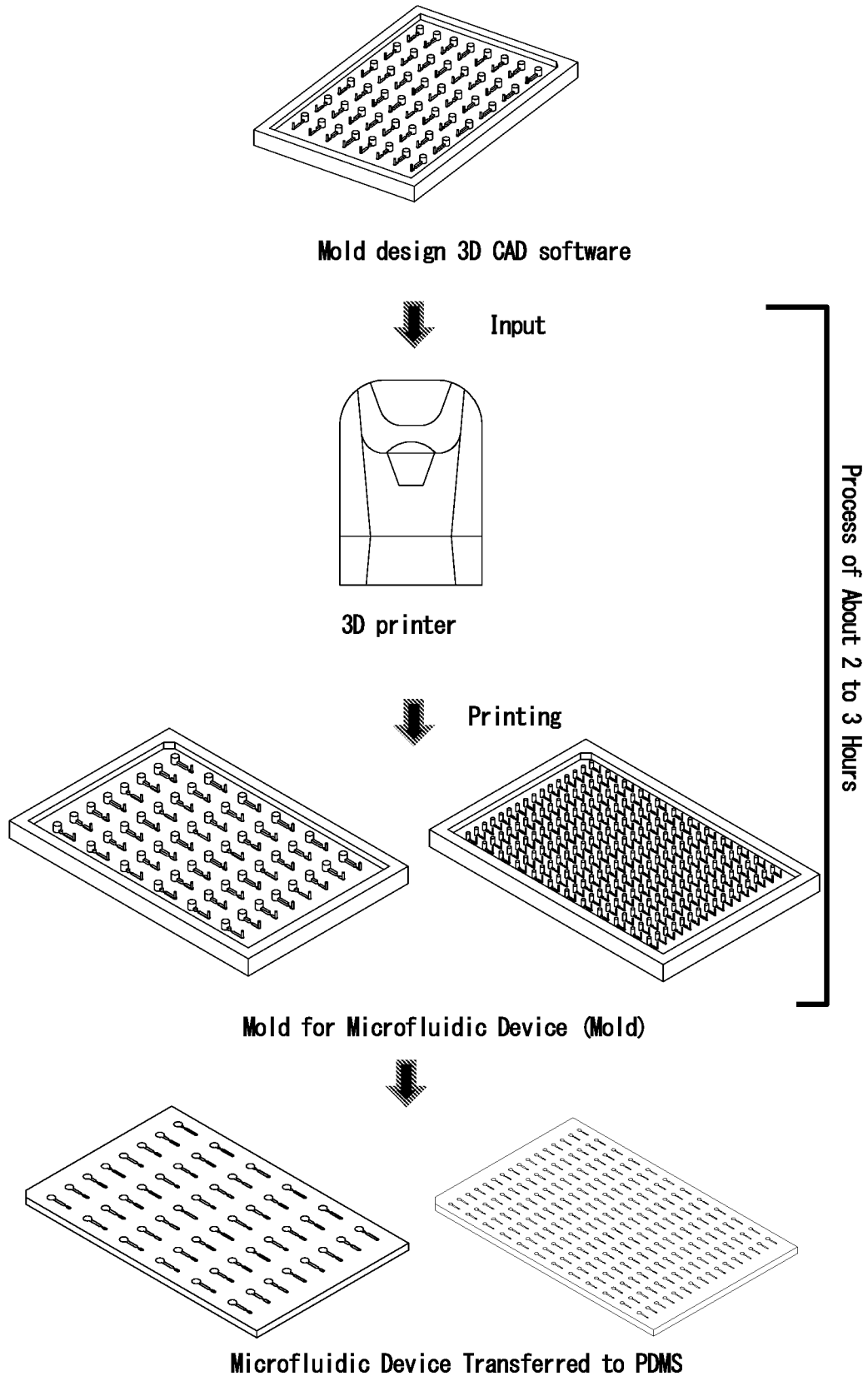
FIG. 4: The steps for preparing a microfluidic device. A desired design was drawn by using 3D-CAD, and a mold of the structure was printed by a 3D printer. It is also possible to prepare a mold by typical photolithography or by using an injection-molding mold for mass production. A PDMS liquid material (a mixture of a base and a curing agent) was poured into the mold to prepare a device made of PDMS with a µFD structure.

The microfluidic device of the present invention can be obtained, for example, by forming a mold using a 3D printer as shown in FIG. 4, pouring a starting material into the mold, and solidifying the material, for example, by polymerization. Although FIG. 4 shows a microfluidic device made of PDMS, a person skilled in the art can easily produce a microfluidic device made of other materials in accordance with FIG. 4 and a known method.

The microfluidic device has multiple cell culture chambers, and the device is preferably for use in a high-throughput fashion. Thus, a single device can have about 10 to 400 chambers, for example, 16, 48, 96, or 384 chambers.

Figure 5:
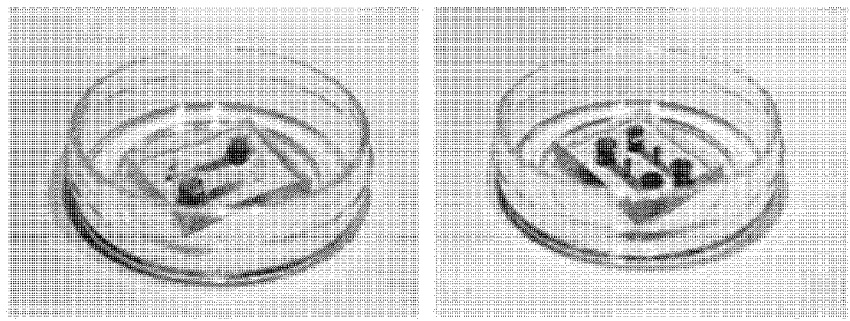
FIG. 5: Examples of the microfluidic device for a 3D culture according to the present invention. Left: there is one large opening for cell introduction and medium replacement, and one small opening as an outlet, with the two large and small openings connected through a cell culture chamber. A medium, growth factors, and the like are introduced from the large opening to thereby form the concentration gradients. Right: two large openings are connected to a cell culture chamber. It is possible to homogeneously culture cells in the cell culture chamber.
Figure 6:
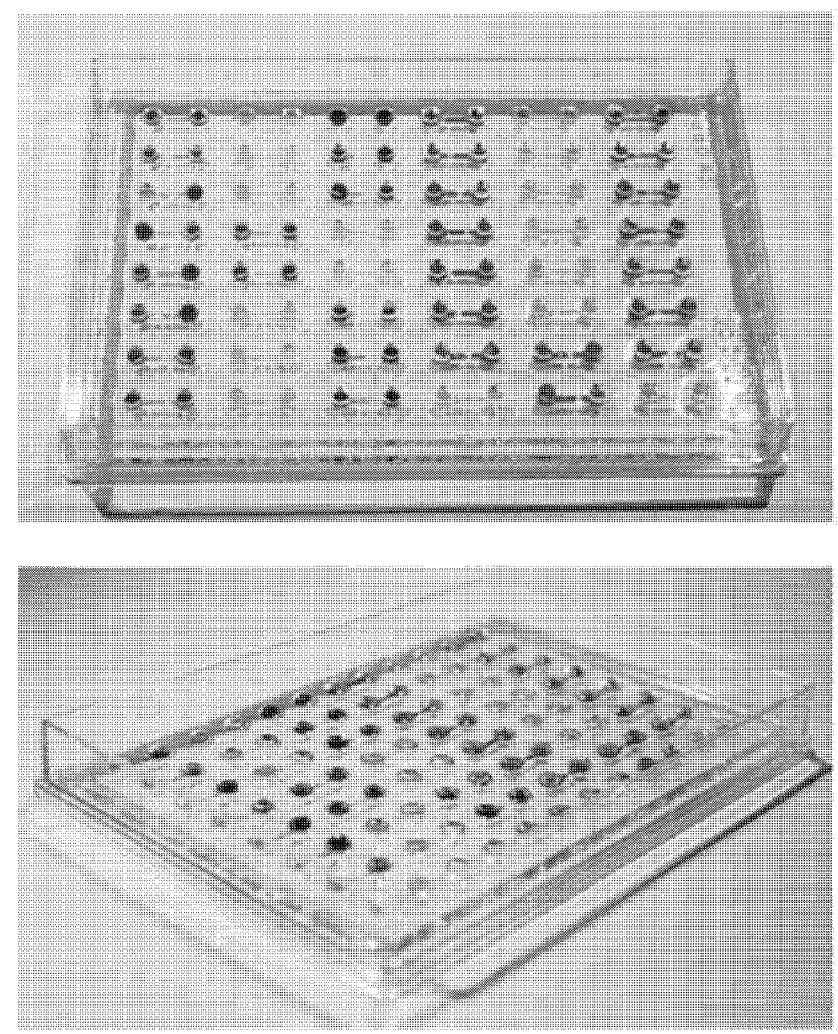
FIG. 6: High throughput screening (HTS) microfluidic device (µFD). The 3D culture of the present invention is also applicable to HTS-µFD.
Figure 7:
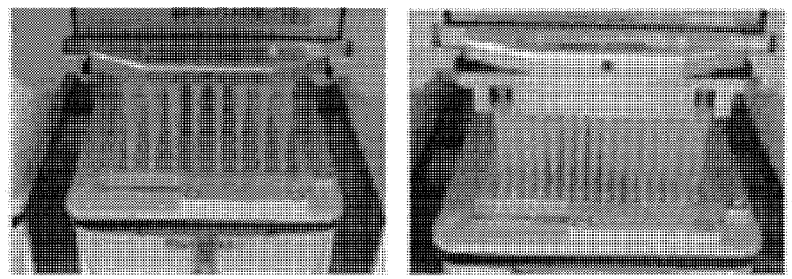
FIG. 7: Liquid feeding with an autoinjector. In 96-well (left figure) and 384-well (right figure) formats, the correspondence between the pipette tips and HTS-µFD was confirmed.
Figure 8:
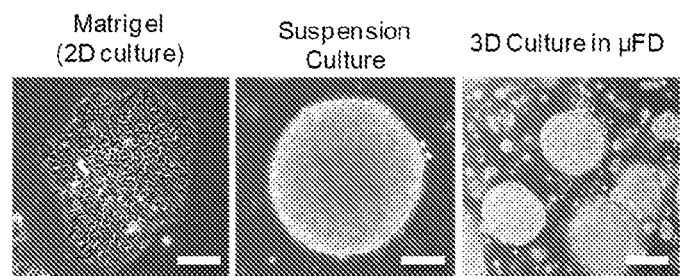
FIG. 8: A photograph of human pluripotent stem cells that were 3D-cultured in a µFD, and the shape of the colonies formed of human pluripotent stem cells cultured by different techniques. When cultured in a µFD or a suspension culture, the human pluripotent stem cells formed spherical cell aggregates. The traditional 2D culture formed a single-layered colony.
Figure 21:
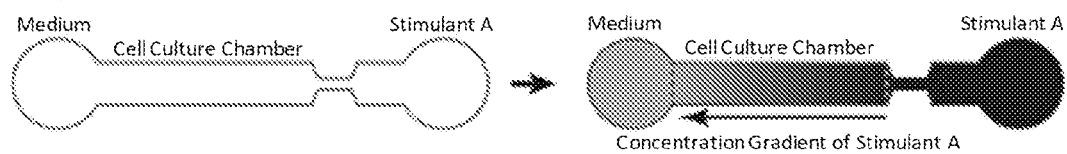
FIG. 21: Drawings of the designs of the cell culture chamber in a microfluidic device. Multiple concentration gradients can be formed in a single cell culture chamber. Various stimuli can be applied depending on the design of the microfluidic device.
Figure 21:
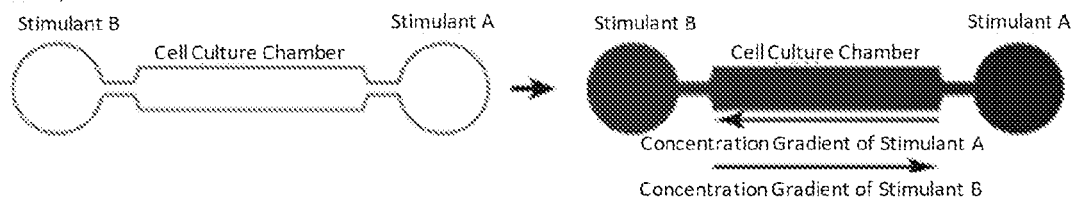
Figure 21:
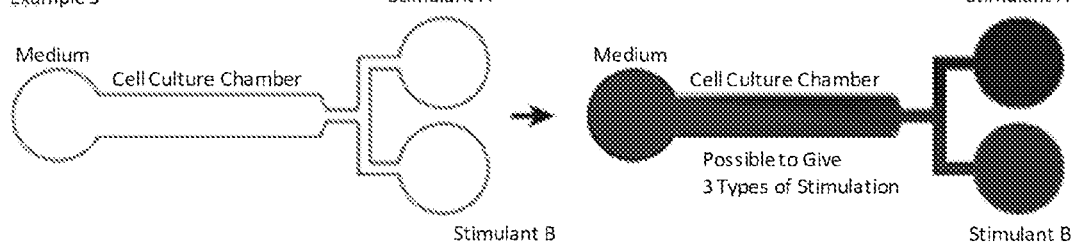

In the microfluidic device of the present invention, the cell culture chamber is connected to at least two openings from which cells or a culture solution can be supplied to the chamber (FIGS. 5 and 21). In the cell culture chamber, cells are 3D-cultured, the culture solution is replaced, and at least one physiologically active substance is supplied in such a manner as to form a concentration gradient or concentration gradients. One device preferably has multiple cell culture chambers. A single device provided with 96 or 384 cell culture chambers can be used as a high throughput device (FIGS. 4, 6, and 7).

It is preferable to cover the upper part of the microfluidic device with a lid to prevent the culture solution from evaporating.

Figure 12:
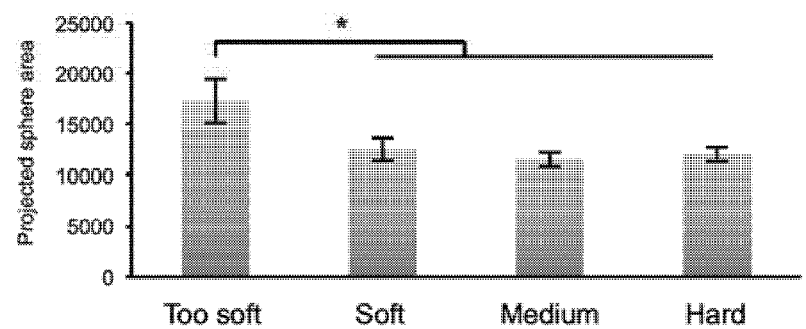
FIG. 12: The "solidity" of the 3D culture environment in a μFD can be changed by the gel concentration.
Figure 13:
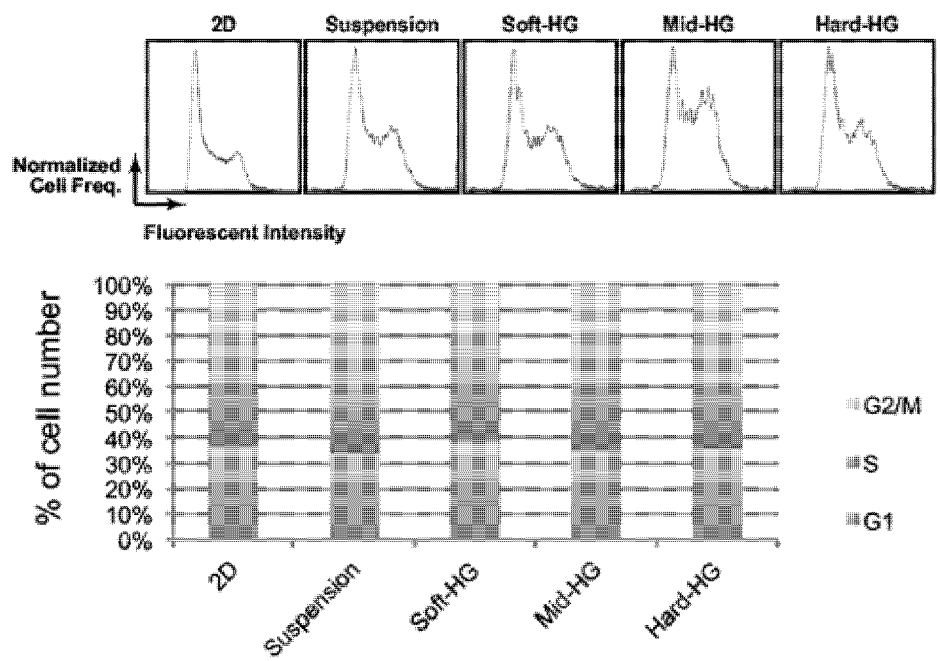
FIG. 13: High throughput screening (HTS) microfluidic device (μFD). As shown in the photograph, screening using a 3D culture is possible. Cell-cycle analysis. Fewer G2/M phase cells were present than those in the cells in a suspension culture.
Figure 14:
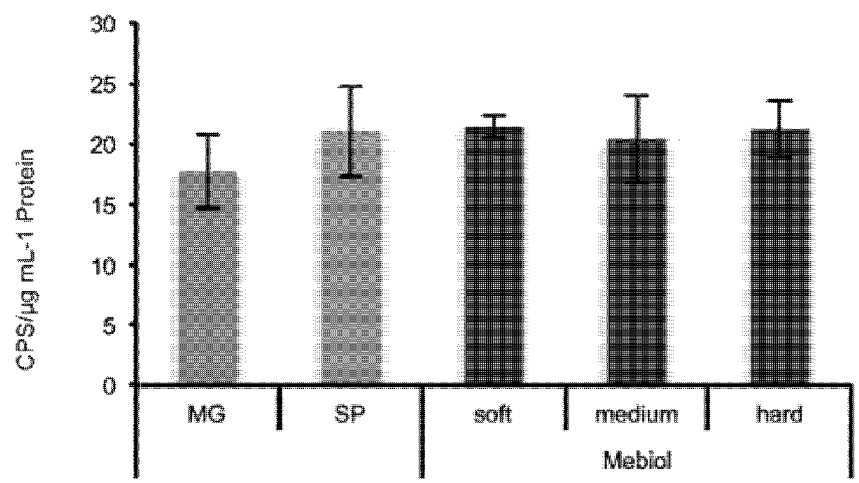
FIG. 14: The evaluation of cell activity (ATP) using a firefly luciferase. In every condition, substantially the same ATP activity was confirmed with no damage to the cells.
Figure 15:
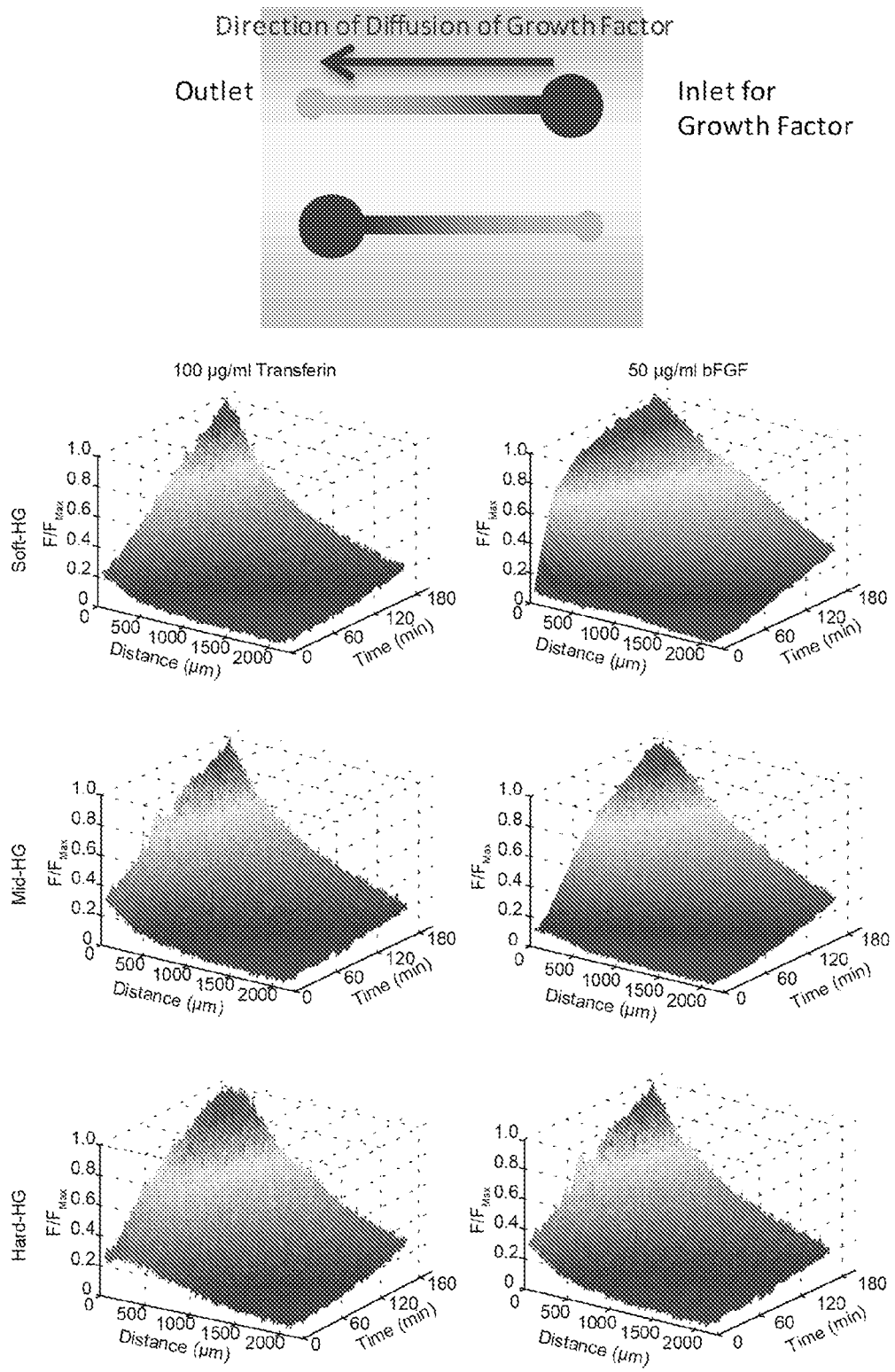
FIG. 15: The measurement of growth factor diffusion in a μFD/hydrogel. The diffusion of bFGF (molecular weight: 17 kDa) and transferrin (molecular weight: 80 kDa) in gels with different degrees of solidity was evaluated. Each factor was fluorescently labeled. Factors with a smaller molecular weight rapidly diffused.
Figure 16:
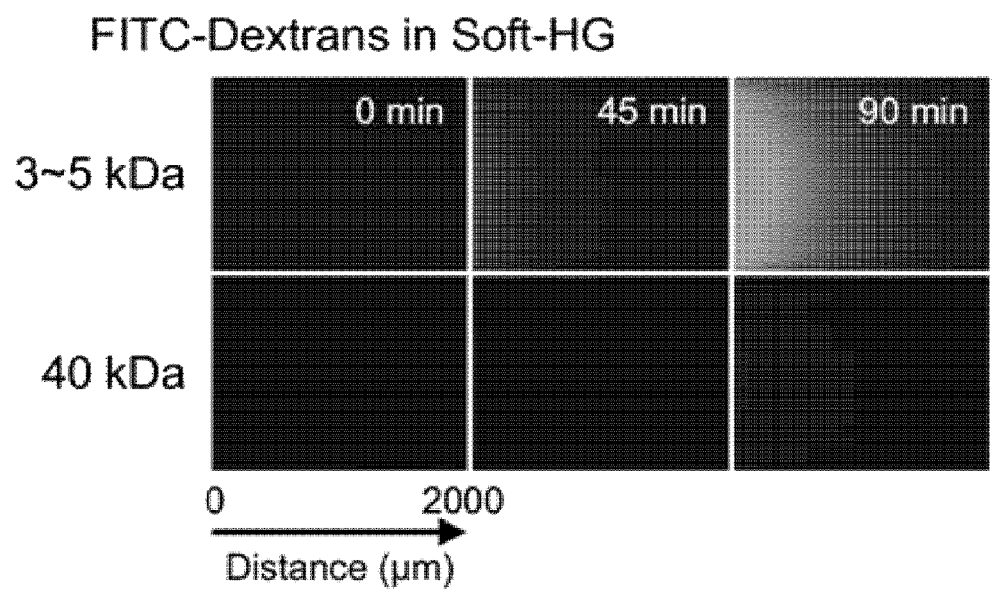
FIG. 16: The diffusion of fluorescently labeled dextran in a μFD+hydrogel (Soft-HG 61 mg mL$^{-1}$). Fluorescently labeled dextran of different molecular weight was prepared, and the way the dextran diffuses was observed with a fluorescence microscope. Larger molecules did not easily diffuse in a hydrogel.
Figure 17:
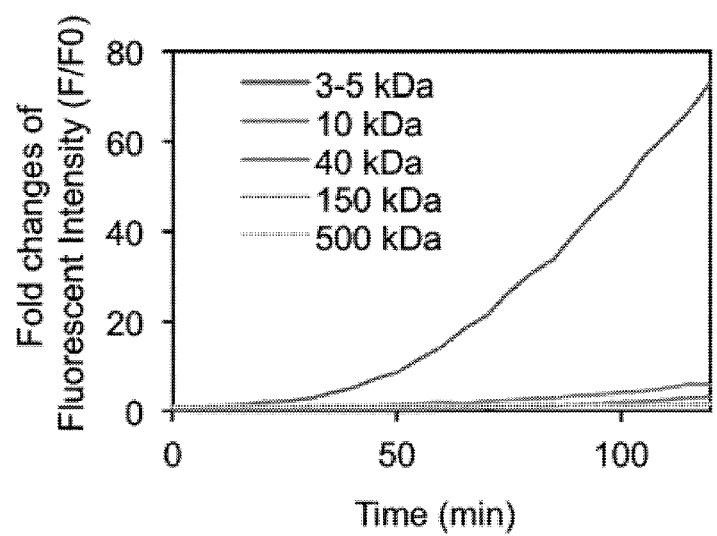
FIG. 17: The diffusion of fluorescently labeled dextran in a μFD+hydrogel (Soft-HG 61 mg mL$^{-1}$). Fluorescently labeled dextran of different molecular weight was prepared, and the way the dextran diffuses was observed with a fluorescence microscope. While the fluorescence intensity was measured, the diffusion of the molecules was quantified. The diffusion decreased in accordance with the molecular weight.
Figure 18:
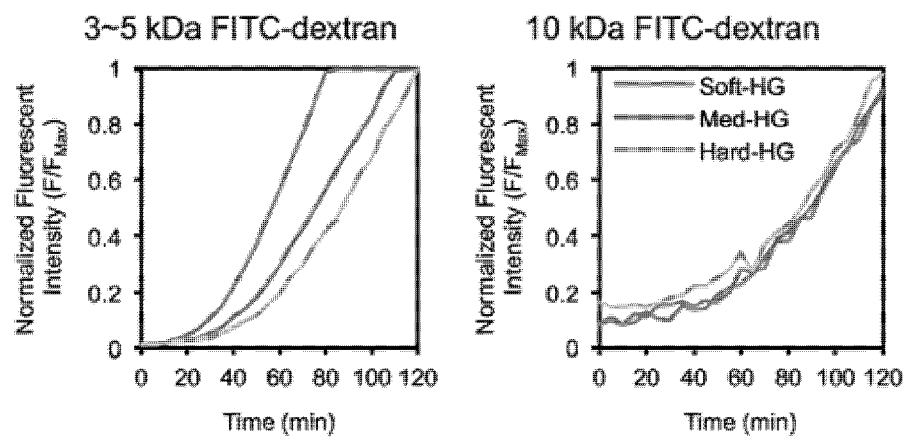
FIG. 18: The diffusion of fluorescently labeled dextran in a μFD+hydrogel (Soft-HG 61 mg mL$^{-1}$). Dextran with a small molecular weight (3 to 5 kDa) was able to rapidly diffuse in a soft gel due to the influence of the solidity of the gel (concentration). However, dextran with a large molecular weight (10 kDa or more) was little affected by the solidity of the gel.

FIG. 15 shows the diffusion of physiologically active substances in hydrogels. FIG. 15 shows that a physiologically active substance introduced from the opening diffuses across the hydrogel, and that the diffusion is affected by the molecular weight of the physiologically active substance. The diffusion rate is also affected by the gel strength (FIG. 18). FIG. 12 shows that the gel strength can be changed by the concentration of the hydrogel, and FIG. 13 shows that the high throughput screening (HTS) microfluidic device (µFD) of the present invention can conduct a cell-cycle analysis. FIG. 14 shows based on the ATP activity that the cells cultured in a 3D culture of the present invention are not damaged. FIGS. 16 and 17 show that the diffusion rate of a large physiologically active substance is slow.

Figure 9:
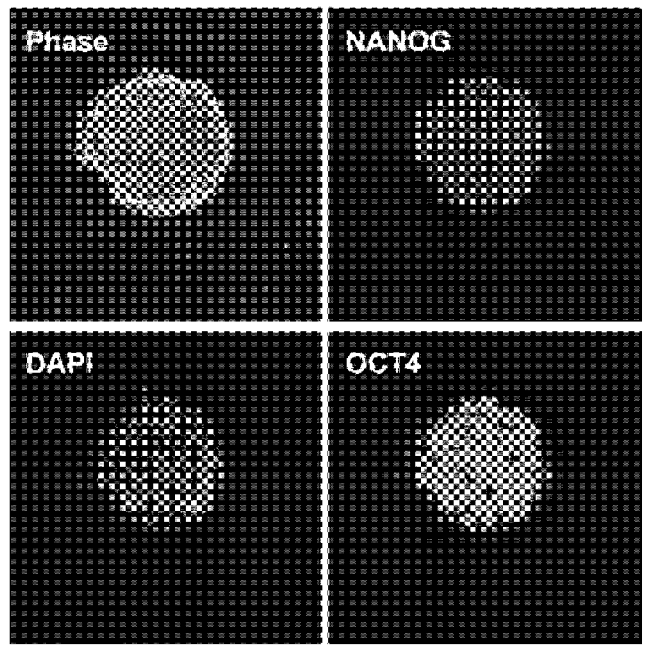
FIG. 9: The confirmation of the expression of human pluripotent stem cell markers (OCT4 and NANOG) by immunofluorescent staining. Both markers exhibited high levels of expression in the human pluripotent stem cells cultured in a μFD.
Figure 10:
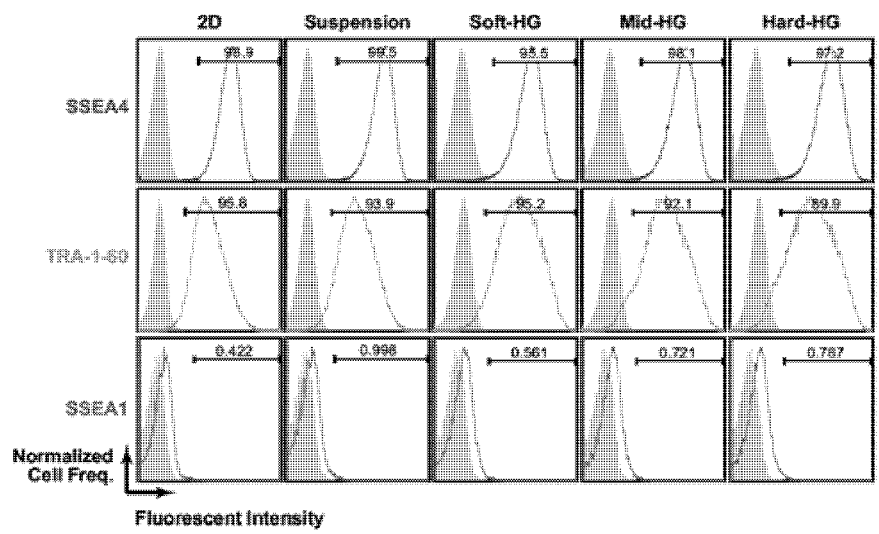
FIG. 10: The confirmation of the expression of human pluripotent stem cell markers (SSEA4 and TRA-1-60) and a differentiation marker (SSEA1) by flow cytometry. A 3D culture was performed by using three gels with different degrees of solidity (Soft-HG, Mid-HG, and Hard-HG). In every environment, the stem cell markers exhibited high levels of expression, and the differentiation marker did not exhibit the expression.
Figure 11:
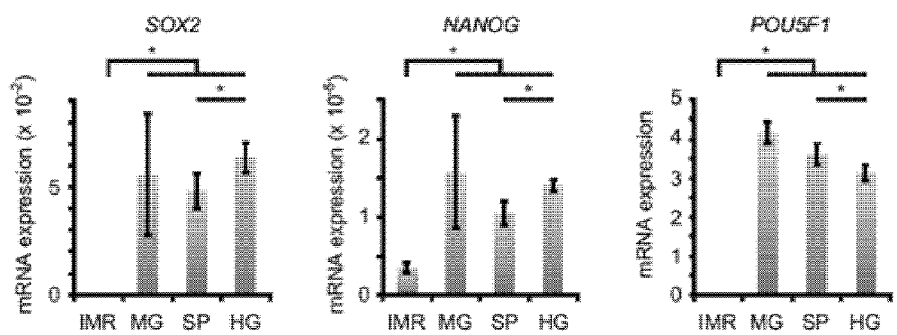
FIG. 11: The confirmation of the expression of human pluripotent stem cell markers (SOX2, NANOG, and POU5F1 (OCT4)) by quantitative PCR. In every 3D culture (HG), the stem cell markers exhibited high levels of expression as in the typical 2D culture (matrigel MG).
Figure 19:
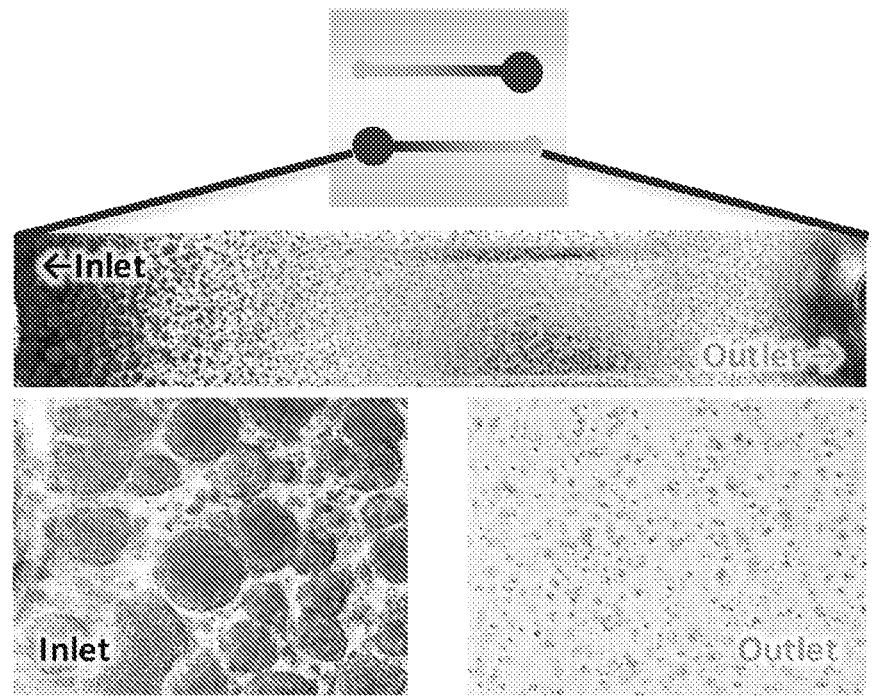
FIG. 19: Colony formation efficiency of human pluripotent stem cells depending on the growth factor concentration gradient in a μFD/hydrogel. Colonies were efficiently formed near the inlet in which the concentration of the growth factor was high.
Figure 20:
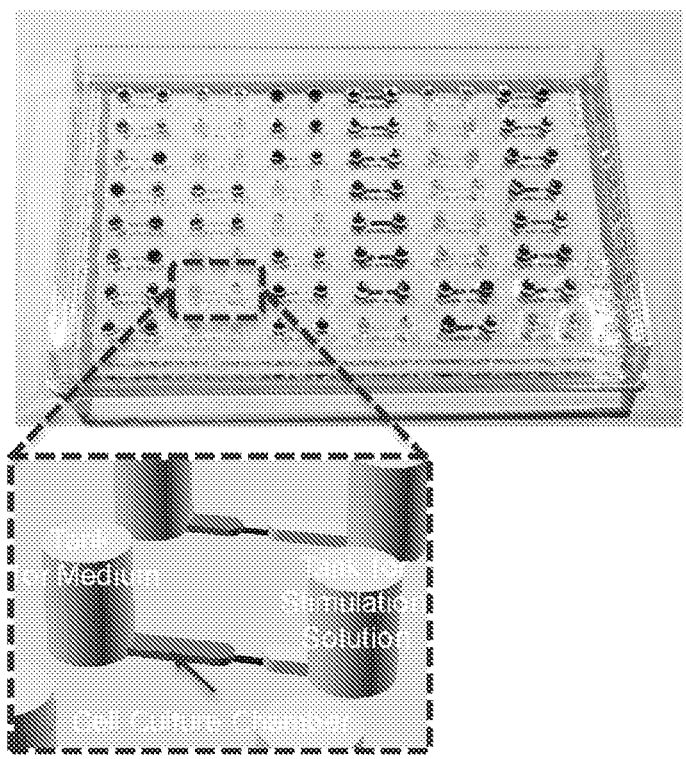
FIG. 20: High throughput screening (HTS) microfluidic device (μFD) and a conceptual diagram of the microfluidic part. Cells mixed with a hydrogel were introduced into the cell culture chambers. It is possible to form a concentration gradient of a cell stimulant by connecting the tank for the medium for cell maintenance and the tank for the cell stimulation solution to each cell culture chamber.

In a preferable embodiment of the present invention, a microfluidic device with multiple cell culture chambers is formed, and cells are cultured in the chambers. The markers of the cultured pluripotent stem cells are expressed (FIGS. 9 to 11). The action of a physiologically active substance, such as the colony formation efficiency of the pluripotent stem cells, was affected by the concentration gradient (FIG. 19). FIG. 20 shows an embodiment in which the channel between the stimulation solution tank for supplying a physiologically active substance and the cell culture chamber is narrow so that the physiologically active substance is supplied little by little, thereby forming a concentration gradient, and in which the medium tank (the opening) is directly connected to the cell culture chamber so that the medium can be efficiently supplied and replaced. As shown in FIG. 21, one, or two or more openings for supplying a physiologically active substance (stimulant) may be provided, and multiple substances can be supplied to the 3D-cultured cells at any given timing.

The height of the cell culture chamber is about 100 to 1,000 µm, the width is about 100 to 1,000 µm, and the depth is about 1,000 to 10,000 µm. The length of the microchannel that connects the cell culture chamber to the opening is about 1,000 to 10,000 µm, and the diameter of the microchannel is about 100 to 1,000 µm.

The size of the opening is larger than the diameter of the microchannel. Setting the size of the opening close to the diameter of the cell culture chamber is effective for introducing cells into the chamber. When the opening is connected to the cell culture chamber through a microchannel that is narrower than the diameter of the opening and the diameter of the chamber, the diffusion of a physiologically active substance is restricted, making it easy to form a concentration gradient of the physiologically active substance.

The chamber has multiple (typically two) openings. When a fresh culture solution is provided from one opening of the chamber, the old culture solution is discharged from the other opening through the microchannel, replacing the culture solution.

Examples of materials for the microfluidic device include polysiloxane-based polymers, such as polydimethylsiloxane (PDMS), and diphenyl siloxane; polyolefins, such as silicone resin/silicone rubber, natural rubber, synthetic rubber, polyethylene terephthalate (PET), polymethyl methacrylate (PMMA), polymethyl acrylate (PMA), polycarbonate, polyethylene, and polypropylene; homopolymers and copolymers, such as polyurethane, polystyrene, fluorinated polymer (e.g., PTFE and PVdF), polyvinyl chloride, polymethyl hydrogen siloxane, copolymers of dimethyl siloxane with methyl hydrogen siloxane; and blends of these materials. Polysiloxane-based polymers are preferable, and PDMS is more preferable. A microfluidic device with high transparency is preferable because of the ease of evaluating the 3D cell culture. The microfluidic device is preferably excellent in gas permeability, for example, for oxygen and carbon dioxide.

The microfluidic device can be produced by forming a desired mold, and pouring any polymer listed above or its starting material into the mold. The method for producing the mold is not particularly limited, but the method using a 3D printer is preferable.

The microfluidic device has multiple cell culture chambers, and the device is preferably for use in a high-throughput fashion. Thus, a single device can have about 10 to 400 chambers, for example, 16, 48, 96, or 384 chambers.

The chamber preferably contains a small amount of a culture solution and a small number of cells. A single chamber can retain, for example, 100 to 2,000 µL of a liquid or gel in its space. A cell culture can be performed by supplying cells and a culture solution to the space.

The number of cells cultured in one single chamber is typically about $5 \times 10^5$ to $0.5 \times 10^5/cm^2$. The shape of the space for culture in the chamber is not particularly limited as long as 3D culture is possible. Examples include a cylindrical shape, a square tube shape, and an elliptic cylindrical shape.

In a particularly preferable embodiment, the present invention is supported by the following developments (a) to (d).

(a) Development of a Novel Microfluidic Device for a 3D Culture

The "extracellular microenvironment," which plays an important role in the regulation of cell function in vivo, was difficult to reproduce in a traditional in vitro experimental system. This is because the traditional cell culture dishes can treat only a large space (about mm to cm), and were not experimental systems on a µm scale required for the reproduction of the extracellular microenvironment. However, microfluidic devices have enabled the production of a very small space on a µm scale, taking a step closer to the reproduction of the extracellular microenvironment.

Nonetheless, in the experimental cell system of the previous microfluidic devices, cells are merely cultured on a plane surface of a culture substrate (e.g., glass or plastic) in a microfluidic device, and this is not truly a 3D culture. To realize a real 3D culture, the present invention uses a hydrogel as an extracellular substrate. The hydrogel is a gel that is formed when a polymer contains water. Mixing a culture solution with the polymer enables the culture of cells in the gel. In addition, changing the polymer concentration allows adjustment of the solidity of the gel, making it possible to investigate "the influence of the solidity of the environment exerted on cells," which was previously difficult to examine. The diffusion of a substance in the gel depends on the molecular weight. It is also possible to evaluate the diffusion of a substance in the gel and the cell response to the diffusion.

(b) Development of a 3D Culture Method for Human ES/iPS Cells Using Phase Transition Hydrogel In the cell culture method using a hydrogel, it has been extremely difficult to collect cells without causing damage to the cells. Thus, in a preferable embodiment of the present invention, a reversible-phase-transition hydrogel is used to solve this problem. Although being less adhesive to cells, this hydrogel shows no cytotoxicity, and can be used as a support carrier for a 3D culture. The hydrogel forms a gel in a cell culture environment (37° C.), and transforms into a liquid at a low temperature (20° C.) or less. Thus, the hydrogel can be introduced into or removed from the microfluidic device without affecting the cells.

(c) Development of a Technique for Preparing a Mold for a Microfluidic Device Using a 3D Printer Although the µFD has various advantages in cell biology, it takes time to prepare the mold in the process of producing the device.

The present invention encompasses the use of a 3D printer to produce a mold. 3D printers can print an intricate 3D structure, and 3D printers for household use are now commercially available. The 3D printer with an X-Y resolution of 50 µm and a Z resolution of 15 µm used in the present invention is sufficient for producing the microfluidic device for a cell culture. The material used for the mold is a plastic resin with thermotolerance of 70° C., which is a relatively low temperature. Thus, when the design was transferred to polydimethylsiloxane (PDMS), which is a material for the microfluidic device, the temperature was maintained at 65° C.

(d) Development of a High-Throughput Screening System Combined with a Microfluidic Device To efficiently identify physiologically active substances (stimulants) suitable for differentiation while maintaining the function of pluripotent stem cells, the present invention developed a high-throughput screening system combined with the microfluidic device. Physiologically active substances can be supplied to a 3D culture in such a manner as to form concentration gradients. The high-throughput screening system using the device of the present invention can determine what physiologically active substances are suitable to be supplied in what concentration gradient for development and differentiation of cells.

EXAMPLES

The following describes the present invention with reference to the Examples in more detail.

Example 1: Method for Producing a Microfluidic Device Using a 3D Printer (1) Materials
SYLGARD® 184 Silicone Elastomer kit (base, curing agent)(Dow Corning)
Nunc OmniTray (Thermo scientific 165218)
Glass Bottom Dish (Iwaki Glass Co. Ltd.)
3D Printer AGILISTA (Keyence)
Desiccator
Corona Fit CFG-500 (Shinko Electric & Instrumentation Co., Ltd.)
3D-CAD (AutoCAD, Blender, and others)
(2) Operation Procedure
Preparation of Mold
1. A mask of a mold design, which will be a mold for the microchannel structure, is prepared by using 3D image graphics software (3D-CAD).
2. The mold design is converted into an stf file.
3. The stf file is transferred to the 3D printer and printed.
Preparation of PDMS with a Microchannel Structure
1. A silicone elastomer base is mixed with a curing agent in a ratio of 10:1 (weight ratio) using a stirrer (PDMS mixture).
2. The PDMS mixture is poured into the mold printed by the 3D printer.
3. Degasification is performed with a desiccator for 30 minutes.
4. Heating is performed in an oven at 65° C. overnight.
5. PDMS is collected from the mold.
Preparation of a Microfluidic Device (HTS-µFD, HTNS-µFD)
1. An OmniTray or glass bottom dish is treated with a corona discharge (using, for example, Corona Fit CFG-500).
2. The PDMS is surface-treated with corona.
3. The OmniTray or glass bottom dish is adhered to the PDMS.
4. Heating is performed in an oven at 65° C. overnight.
5. The heated product is stored in a desiccator until use.

Example 2: A 3D Culture Method for Human Pluripotent Stem Cells Using Mebiol Gel (Phase Transition Gel)

(1) Materials
Mebiol gel, Mebiol Inc., PMW20-1001 (10 mL for dilution)
mTeSR1
Veritas Corporation, ST-05850
Y-27632
Wako Pure Chemical Industries, Ltd.
250-00513 (5 mg) TrypLE Express (1×), Phenol Red Life technologies 12605028 (500 mL)
(2) Operation Procedure
Dissolution of Mebiol Gel
The weight of the Mebiol gel was measured in its dry form, and 6 to 10 mL of mTeSR1 was added to 10 mL of the Mebiol gel for dilution. The mixture was allowed to stand at 4° C. overnight to dissolve the mixture. The concentration of the Mebiol gel in this experiment is shown below.
Soft 61 mg/mL
Medium 75 mg/mL
Hard 91 mg/mL Making 3D Culture of Human Pluripotent Stem Cells
1. The fluidic device is sterilized with UV irradiation for 15 minutes.
2. An mTeSR1 medium containing Y-27632 at a final concentration of 10 µM is prepared.
3. The cells on MEF or Matrigel are rinsed with D-PBS(−) twice.
4. TrypLE Express is added thereto, and the mixture is allowed to stand at 37° C. for 3 to 5 minutes.
5. TrypLE Express is removed by suction.
6. When cells on MEF are used, the cell layer is rinsed in the medium to remove the torn MEF.
7. The cells are collected in mTeSR1+Y-27632 medium.
8. The cell suspension is pipetted to obtain a single cell preparation.
9. Centrifugation is performed at 1,000 rpm for 3 minutes.
10. The supernatant is removed by suction.
11. The cell pellets are suspended again in mTeSR1+Y-27632 medium.
12. The number of cells is measured.
13. $4 \times 10^5$ cells are dispensed into a new tube.
14. Centrifugation is performed at 1,000 rpm for 3 minutes.
15. The supernatant is removed by suction.
(The following operations are performed on ice to prevent the gel from solidifying, and the pipette tips for use are also cooled on ice.)
16. The cell pellets are suspended in 100 to 200 µL of Mebiol gel (dissolved in mTeSR1) ($4 \times 10^5$ cells/100 to 200 µL).
17. At this stage, Y-27632 at a final concentration of 10 µM is added to the Mebiol gel.
18. The cell-Mebiol gel suspension is introduced into the fluidic device cooled on ice (2 to $4 \times 10^4$ cells/10 µL)
19. The device is allowed to stand at 37° C. for 5 minutes to form a gel.
20. An mTeSR1+Y-27632 medium is added to the medium supplier on the device.
21. To prevent drying, sterile distilled water is added to the dish.
22. The next day, the medium is replaced with an mTeSR1+Y-27632 medium, and the following days, the medium is replaced with an mTeSR1 medium once a day.
Collection of Cells from a Mebiol Gel
1. The old medium in the medium supplier is removed.
2. The device is allowed to stand on ice for 5 minutes.
3. A new medium is added to the fluid to dilute the gel.
4. The cells are collected from the fluid.

The invention claimed is:
1. A method of a 3D cell microculture using a microfluidic device having one or more cell culture chambers including one or more openings and one or more tanks connected to the one or more cell culture chambers through the one or more openings, comprising:
introducing a hydrogel into the one or more cell culture chambers, the hydrogel forming a three-dimensional gel having a certain degree of solidity for a highly biocompatible environment;
introducing predetermined cells to be cultured in a uniformly distributed manner in the one or more cell culture chambers; and
supplying at least one physiologically active substance from the one or more tanks to the one or more cell culture chambers through the one or more openings in such a manner as to form a concentration gradient or concentration gradients in the one or more culture chambers.
2. The method of a 3D cell microculture using a microfluidic device according to claim 1, further comprising forming a three-dimensional gel (3D-gel) cell support carrier from the hydrogel, wherein the concentration gradient or the concentration gradients of the physiologically active substance are formed by the 3D-gel cell support carrier due to diffusion over the 3D-gel cell support carrier.

3. The method of a 3D cell microculture using a microfluidic device according to claim 1, wherein the hydrogel is fluidized prior to introducing into the one or more cell culture chambers.

4. The method of a 3D cell microculture using a microfluidic device according to claim 1, wherein the hydrogel and the predetermined cells are introduced substantially at the same time into the one or more cell culture chambers.

5. The method of a 3D cell microculture using a microfluidic device according to claim 1, further comprising, adjusting the solidity of the three-dimensional gel.

6. The method of a 3D cell microculture using a microfluidic device according to claim 1, wherein the hydrogel is a phase transition hydrogel.

7. The method of a 3D cell microculture using a microfluidic device according to claim 6, wherein the phase transition hydrogel includes any combination of chitosan gel, collagen gel, gelatin gel, peptide gel, fibrin gel, starch, pectin, hyaluronic acid, alginic acid, fibronectin, vitronectin, laminin, alginate, and fibroin.

8. The method of a 3D cell microculture using a microfluidic device according to claim 6, wherein the phase transition hydrogel is a temperature-sensitive phase transition hydrogel and is solidified into the three-dimensional gel based upon a temperature change.

9. The method of a 3D cell microculture using a microfluidic device according to claim 1, wherein a mixture of the predetermined cells and the hydrogel is introduced into the one or more cell culture chambers.

10. The method of a 3D cell microculture using a microfluidic device according to claim 9, further comprising, adjusting the solidity of the three-dimensional gel.

11. The method of a 3D cell microculture using a microfluidic device according to claim 1, wherein the predetermined cells include pluripotent stem cells including human ES and iPS cells.

12. The method of a 3D cell microculture using a microfluidic device according to claim 1, wherein a growth factor is supplied at a predetermined concentration from the one or more tanks into the one or more cell culture chambers.

13. The method of a 3D cell microculture using a microfluidic device according to claim 1, further comprising,
deforming the three-dimensional gel into the hydrogel; and
harvesting the cells from the one or more cell culture chambers.

14. The method of a 3D cell microculture using a microfluidic device according to claim 13, wherein the three-dimensional gel is deformed by adjusting a temperature in the one or more cell culture chambers.

15. The method of a 3D cell microculture using a microfluidic device according to claim 13, wherein the three-dimensional gel is deformed by decreasing a concentration of the gel.

16. The method of a 3D cell microculture using a microfluidic device according to claim 13, wherein the three-dimensional gel is deformed by introducing calcium ions.

17. The method of a 3D cell microculture using a microfluidic device according to claim 1, wherein a plurality of the physiologically active substances is supplied to same one of the culture chambers through a plurality of the openings in such a manner as to form a plurality of the concentration gradients of the physiologically active substances over the three-dimensional gel due to diffusion.

18. The method of a 3D cell microculture using a microfluidic device according to claim 1, wherein the concentration gradients are in substantially the same direction over the three-dimensional gel.

19. The method of a 3D cell microculture using a microfluidic device according to claim 1, wherein the concentration gradients are in substantially different directions over the three-dimensional gel.

20. The method of a 3D cell microculture using a microfluidic device according to claim 1, wherein each of the concentration gradients depends upon the solidity of the three-dimensional gel.

21. The method of a 3D cell microculture using a microfluidic device according to claim 1, wherein each of the concentration gradients depends upon the molecular weight of the physiologically active substance.

22. The method of a 3D cell microculture using a microfluidic device according to claim 1, wherein each of the concentration gradients depends upon a combination of the solidity of the three-dimensional gel and the molecular weight of the physiologically active substance.

23. A microfluidic device for cell culture, comprising:
at least one cell culture chamber in a predetermined width, length and depth having a first opening located at one end and a second opening located at the other end along the length, the cell culture chamber containing predetermined cells to be cultured;
at least one first source connected to the cell culture chamber for supplying at least one of predetermined materials to the cell culture chamber through the first opening; and
at least one second source connected to the cell culture chamber for supplying at least one of the predetermined materials to the cell culture chamber through the second opening,
wherein the first opening is unequal to the second opening in size.

24. The microfluidic device for cell culture according to claim 23, wherein the first source is larger than the second source in volume.

25. The microfluidic device for cell culture according to claim 23, wherein the first opening is an inlet for supplying the one of predetermined materials to the cell culture chamber while the second opening is an outlet for removing the one of predetermined materials from the cell culture chamber.

26. The microfluidic device for cell culture according to claim 23, wherein the first source is a first tank that is directly connected to the cell culture chamber through the first opening.

27. The microfluidic device for cell culture according to claim 26, wherein the second source is a second tank that is connected to the cell culture chamber through the second opening.

28. The microfluidic device for cell culture according to claim 23, wherein the second source has a plurality of sources each of which is connected to a respective one of channels that are connected to the cell culture chamber through the second opening.

29. The microfluidic device for cell culture according to claim 23, wherein the first opening is approximately equal to the width of the cell culture chamber.

30. The microfluidic device for cell culture according to claim 23, wherein the first opening is less than the width of the cell culture chamber.

31. The microfluidic device for cell culture according to claim 23, wherein the second opening is approximately equal to the width of the cell culture chamber.

32. The microfluidic device for cell culture according to claim 23, wherein the second opening is less than the width of the cell culture chamber.

33. The microfluidic device for cell culture according to claim 23, wherein the cell culture chamber has a volume of from about 0.5 µL to about 10 µL.

34. A microfluidic device for cell culture, comprising:
- at least one cell culture chamber having a predetermined first width, first length and first depth;
- a three-dimensional gel (3D-gel) cell support carrier having a certain degree of solidity made of a hydrogel for a highly biocompatible microenvironment containing predetermined cells in a uniformly distributed manner in the cell culture chambers;
- an inlet tank directly connected to the cell culture chamber for supplying a material to the cell culture chamber through a first opening; and
- an outlet tank directly connected to the cell culture chamber for removing the material from the cell culture chamber through a second opening, wherein the inlet is larger than the outlet while both the inlet and the outlet are larger than the cell culture chamber.

* * * * *